United States Patent
Eckstein et al.

(10) Patent No.: US 11,155,842 B2
(45) Date of Patent: Oct. 26, 2021

(54) PROCESS FOR PREPARING SPHINGOLIPIDS

(71) Applicant: Evonik Operations GmbH, Essen (DE)

(72) Inventors: Marrit Friederike Eckstein, Essen (DE); Monica Desiree van Logchem, Zevenbergen (NL); Hans Henning Wenk, Mülheim an der Ruhr (DE); Annika Schrader, Bremen (DE); Ursula Maczkiewitz, Essen (DE); Claudia Hierath, Essen (DE); Sunay Karacocuk, Herne (DE); Andreas Seifert, Bottrop (DE)

(73) Assignee: Evonik Operations GmbH, Essen (DE)

( * ) Notice: Subject to any disclaimer, the term of this patent is extended or adjusted under 35 U.S.C. 154(b) by 129 days.

(21) Appl. No.: 16/355,981

(22) Filed: Mar. 18, 2019

(65) Prior Publication Data

US 2019/0300917 A1   Oct. 3, 2019

(30) Foreign Application Priority Data

Mar. 29, 2018  (EP) .................................... 18164835

(51) Int. Cl.
| | |
|---|---|
| *C12P 13/02* | (2006.01) |
| *A61K 8/68* | (2006.01) |
| *A61K 8/92* | (2006.01) |
| *C07H 15/00* | (2006.01) |
| *A61Q 5/12* | (2006.01) |
| *A61Q 19/00* | (2006.01) |

(52) U.S. Cl.
CPC ............... *C12P 13/02* (2013.01); *A61K 8/68* (2013.01); *A61K 8/92* (2013.01); *C07H 15/00* (2013.01); *A61Q 5/12* (2013.01); *A61Q 19/00* (2013.01); *C12Y 301/01003* (2013.01)

(58) Field of Classification Search
None
See application file for complete search history.

(56) References Cited

U.S. PATENT DOCUMENTS

| | | | |
|---|---|---|---|
| 6,846,940 B2 | 1/2005 | Arbey et al. | |
| 8,647,848 B2 * | 2/2014 | Hollmann | A61Q 19/00 435/129 |
| 2004/0005282 A1 | 1/2004 | Arbey et al. | |
| 2006/0029657 A1 | 2/2006 | Popp et al. | |
| 2007/0087418 A1 | 4/2007 | Mazeaud et al. | |
| 2011/0065801 A1 | 3/2011 | Hollmann et al. | |
| 2011/0077302 A1 | 3/2011 | Hollmann et al. | |
| 2017/0306264 A1 | 10/2017 | Peggau et al. | |
| 2017/0335238 A1 | 11/2017 | Schilling et al. | |
| 2018/0016525 A1 | 1/2018 | Scheuermann et al. | |
| 2018/0023040 A1 | 1/2018 | Schilling et al. | |
| 2018/0344602 A1 | 12/2018 | Schuch et al. | |
| 2019/0040095 A1 | 2/2019 | Lu et al. | |

FOREIGN PATENT DOCUMENTS

| | | |
|---|---|---|
| DE | 199 31 310 A1 | 1/2001 |
| DE | 602 25 239 T2 | 4/2009 |
| WO | 94/26919 A1 | 11/1994 |
| WO | 2011/044207 A2 | 4/2011 |
| WO | 2018/177730 A1 | 10/2018 |

OTHER PUBLICATIONS

European Search Report dated Aug. 8, 2018 in EP 18164835.3 (13 pages).
European Search Report dated Nov. 15, 2019 in EP 19163357.7 (13 pages).
Klostermann et al., U.S. Appl. No. 16/315,744, filed Jan. 7, 2019.
Liebig et al., U.S. Appl. No. 16/312,480, filed Dec. 21, 2018.
Schilling et al., U.S. Appl. No. 16/332,979, filed Mar. 13, 2019.

* cited by examiner

*Primary Examiner* — Anand U Desai
(74) *Attorney, Agent, or Firm* — Taylor English Duma LLP; Philip P. McCann

(57) ABSTRACT

The invention provides a process for preparing sphingolipids, compositions comprising sphingolipids and further components, and for the use of the compositions.

12 Claims, 3 Drawing Sheets

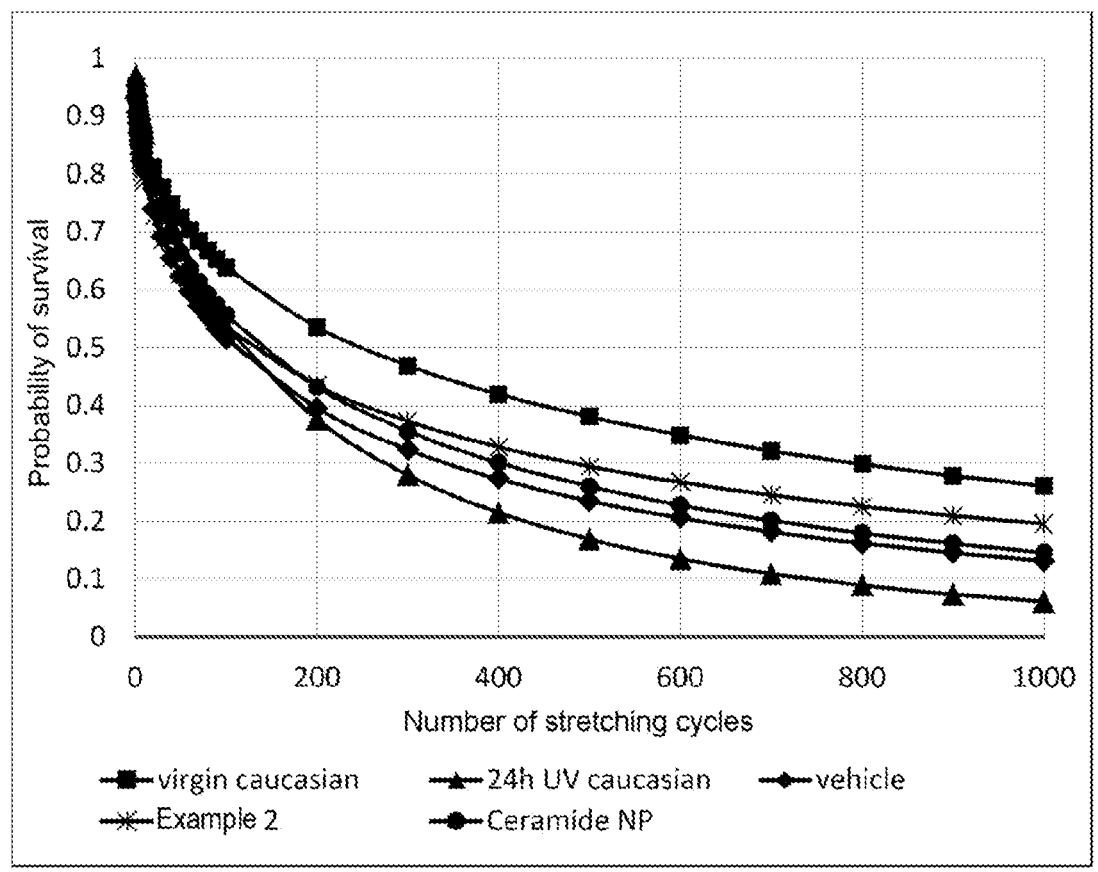
Figure 1: Probability of survival of the individual hairs

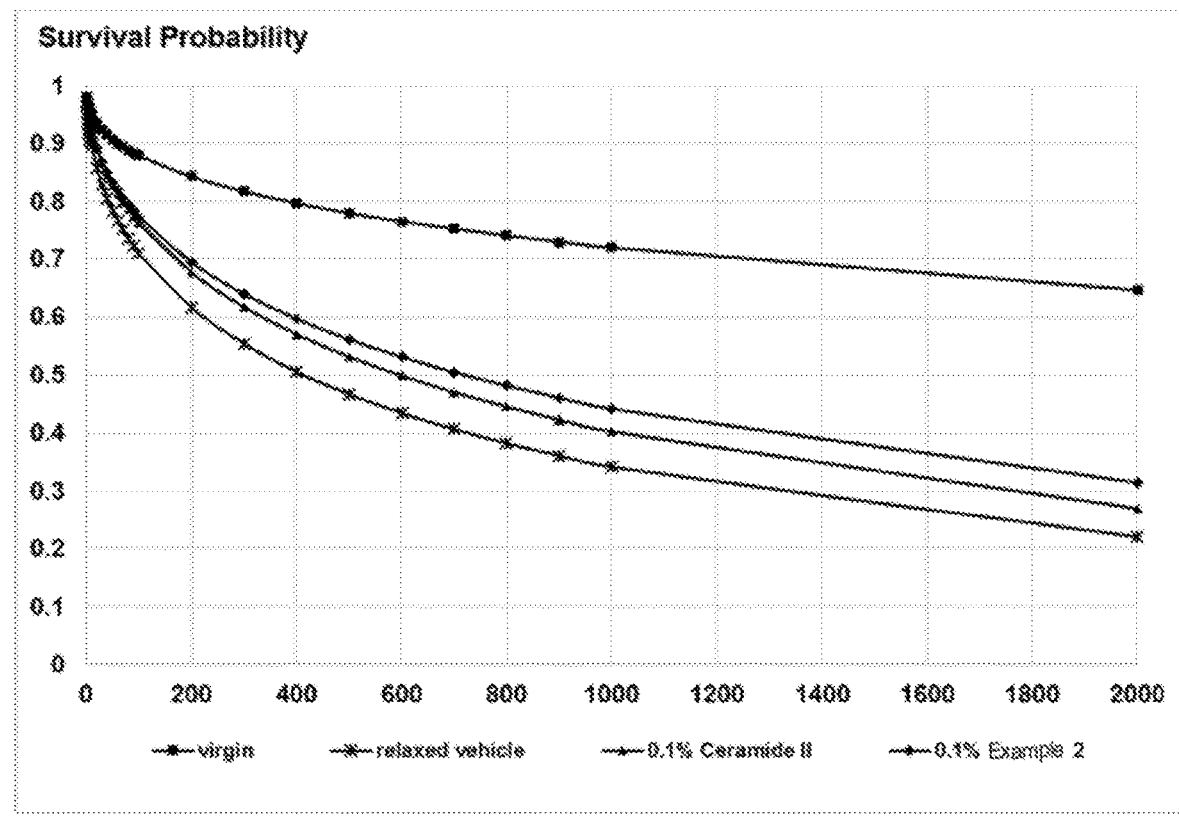
Figure 2: Probability of survival of alkali-straightened hair after treatment with ceramides

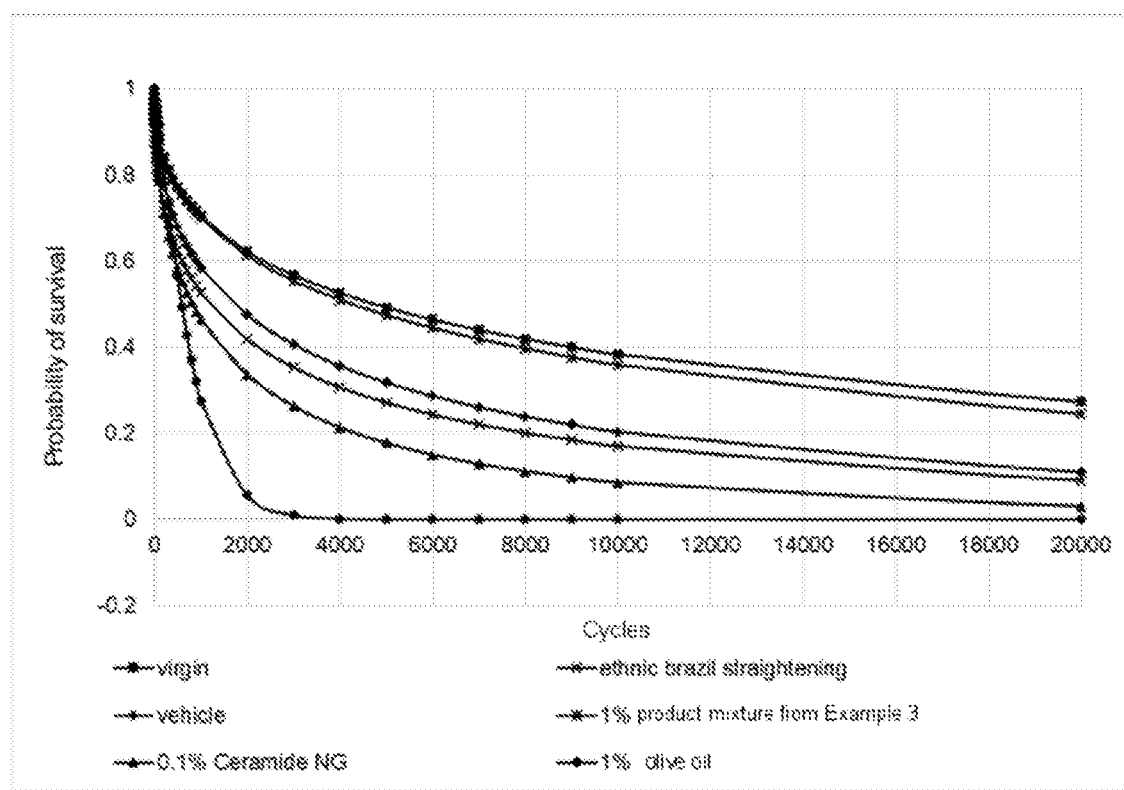
Figure 3: Probability of survival of ethnic hair

PROCESS FOR PREPARING SPHINGOLIPIDS

CROSS REFERENCE TO RELATED APPLICATIONS

This application is a 35 U.S.C. § 119 patent application which claims the benefit of European Application No. 18164835.3 filed Mar. 29, 2018, which is incorporated herein by reference in its entirety.

FIELD

The invention provides a process for preparing sphingolipids, compositions comprising sphingolipids and further components, and for the use of the compositions.

BACKGROUND

US20110077302 discloses a process for biocatalytic preparation of sphingolipids by reacting a lysosphingolipid with carboxylic esters, characterized in that a biocatalyst comprising at least one carboxylic ester hydrolase from the E.C. 3.1.1 enzyme class from an organism from the fungal realm and homologues thereof is used.

US20110065801 discloses a process for biocatalytic preparation of sphingolipids by reacting a lysosphingolipid with glycerides, wherein a biocatalyst comprising at least one carboxylic ester hydrolase from the E.C. 3.1.1 enzyme class is used.

The use of high amounts of solvents and high enzyme concentrations are emphasized as being advantageous in the prior art.

SUMMARY

The problem addressed by the present invention was that of providing an alternative, gentle and industrially applicable route to ceramides in which it is possible to work in a resource-conserving manner.

BRIEF DESCRIPTION OF THE DRAWINGS

FIG. 1 is a graph showing the survival probability of the individual hairs.

FIG. 2 is a graph showing the survival probability of alkali-straightened hair after treatment with ceramides.

FIG. 3 is a graph showing the survival probability of ethnic hair.

DETAILED DESCRIPTION

It has been found that, surprisingly, the process described hereinafter constitutes an excellent alternative to the prior art and surprisingly provides compositions that have advantageous properties.

The present invention therefore provides a process for preparing sphingolipids as described in claim 1.

The invention further provides compositions comprising sphingolipids and further components, and for the use thereof.

One advantage of the process according to the invention is that, by virtue of the very small amounts of solvent and of enzyme used, it is possible to work in a particularly resource-conserving manner. In addition, it has been found that, surprisingly, in the solvent-free conversion, a very small amount of enzyme leads to the best results.

The use of triglycerides under the reaction conditions according to the invention additionally leads to product mixtures that differ from the prior art, for example US20110065801, by the presence of mono- and diglycerides and additionally have special effects, especially in cosmetic applications.

One advantage of the composition according to the invention is that the composition has excellent incorporability into cosmetic oils.

One advantage of the composition according to the invention is that the composition in formulations has superior sensory properties which lead to an improved skin feel and/or hair feel.

It is a further advantage of the composition according to the invention that the composition in formulations stimulates in vitro human follicular dermal papilla cells (HFDPCs) to proliferate, which in vivo equates to stimulation of hair growth.

It is a further advantage of the composition according to the invention that the composition in formulations has improved distributability compared to the individual components.

It is a further advantage of the composition according to the invention that the composition in formulations has improved absorption compared to the individual components.

It is a further advantage of the composition according to the invention that the composition in formulations has reduced oiliness compared to the individual components.

It is a further advantage of the composition according to the invention that the composition in formulations has reduced waxiness compared to the individual components.

It is a further advantage of the composition according to the invention that the composition in formulations has improved glidability compared to the individual components.

It is a further advantage of the composition according to the invention that the composition in formulations has reduced tackiness compared to the individual components.

It is a further advantage of the composition according to the invention that the composition in formulations has improved silkiness/velvetiness compared to the individual components.

The "pH" in connection with the present invention—unless stated otherwise—is defined as the value which is measured for the relevant composition at 25° C. after stirring for five minutes using a pH electrode calibrated in accordance with ISO 4319 (1977).

The accession numbers cited in the context of the present invention correspond to the NCBI protein bank database entries as at Jan. 1, 2017; generally, in the present context, the version number of the entry is identified by ".number", for example "1".

Unless stated otherwise, all percentages (%) given are percentages by mass.

The present invention therefore provides a process for preparing sphingolipids of the general formula I

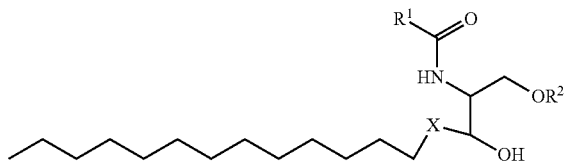

Formula I by reacting a first component, a lysosphingolipid of the general formula II

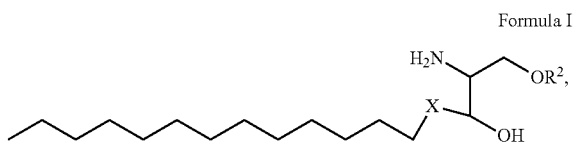

Formula II with a second component, an acyl group donor of the acyl group R¹CO, where $R^1$ represents a linear or branched alkyl chain having 2 to 55 carbon atoms that optionally contains one or more multiple bonds and/or aromatic or heteroaromatic rings, is optionally interrupted by oxygen atoms or ester or amide functionalities and is optionally substituted by at least one further group selected from alkyl, hydroxyl, keto or amine groups, preferably —CH$_2$—Y—CH$_3$ with Y=a carbon-carbon bond or a linear or branched alkylene chain having 1 to 53, especially 6 to 32, carbon atoms that optionally contains one or more multiple bonds and is optionally substituted by at least one hydroxyl group, $R^2$ represents H, phosphocholine, serine, ethanolamine or a sugar, preferably sugar or H, more preferably H, and X represents CH=CH, CH$_2$—CH$_2$ or CH$_2$—HCOH, preferably CH$_2$—CH$_2$, characterized in that the first and second components, based on the overall reaction mixture, account for a total of at least 70% by weight, preferably 90% by weight, especially 95% by weight, and not more than 600 propyl laurate units of at least one carboxylic ester hydrolase from the E.C. 3.1.1 enzyme class per gram of first component are used in the entire reaction mixture, where one propyl laurate unit is defined as the amount of enzyme that synthesizes one μmol of propyl laurate per minute from 1-propanol and lauric acid.

The measured activity of the carboxylic ester hydrolase in propyl laurate units is measured at the temperature optimal for the given enzyme, where "optimal temperature" is understood to mean that temperature at which the enzyme has its highest activity. For lipases A and B with accession number P41365 from *Candida antarctica*, for example, the optimal temperature is 60° C.

The first component used is preferably sphinganine with $R^2$=H and X=CH$_2$—CH$_2$.

Second components used in accordance with the invention may be any acyl group donors. These are, for example, carboxylic esters or carboxylic acids themselves and mixtures thereof.

Preferably in accordance with the invention, the acyl group donor is selected from carboxylic esters, preferably esters based on alkanols and polyols having up to 6 carbon atoms, more preferably having up to 3 carbon atoms, especially preferably glycerol esters.

Preferably in accordance with the invention, the acyl group donor is selected from acyl group donors that provide an acyl group selected from the group of acyl groups of natural fatty acids. Natural fatty acids can be produced on the basis of naturally occurring vegetable or animal oils and have preferably 6-30 carbon atoms, especially 8-22 carbon atoms. Natural fatty acids are generally unbranched and consist of an even number of carbon atoms. Any double bonds have cis configuration. Examples are: caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, linolenic acid, petroselic acid, elaidic acid, arachic acid, behenic acid, erucic acid, gadoleic acid, linolenic acid, eicosapentaenoic acid, docosahexaenoic acid, arachidonic acid.

Especially preferably in accordance with the invention, the acyl group donor is selected from triglycerides, especially natural fats and oils, more preferably selected from the group comprising, preferably consisting of, coconut fat, palm kernel oil, olive oil, palm oil, argan oil, castor oil, linseed oil, babassu oil, rapeseed oil, algal oils, sesame oil, soya oil, avocado oil, jojoba oil, safflower oil, almond oil, cottonseed oil, shea butter, sunflower oil, cupuacu butter and oils having a high proportion of polyunsaturated fatty acids (PUFAS). It is likewise possible with preference to use sorbitan esters, monoglycerides and diglycerides having above-described chain length distributions and modifications.

It is clear that the acyl group donor used determines the $R^1$ radical.

More preferably in accordance with the invention, the first component used is sphinganine with $R^2$=H and X=CH$_2$—CH$_2$, and the second component used is an acyl group donor selected from the group comprising, preferably consisting of, coconut fat, palm kernel oil, olive oil, palm oil, argan oil, castor oil, linseed oil and babassu oil.

According to the invention, the reactants may be present on commencement of the reaction in a molar ratio of first component to second component of 1:0.11 to 1:200 000, preferably to 1:2000. The term "molar ratio" refers here to the molar ratio of lysosphingolipid to the number of acyl groups provided by the acyl group donor. Preference is given to using molar ratios between 1:0.3 and 1:200. Particular preference is given to using molar ratios between 1:1 and 1:50.

In an alternatively preferred embodiment, the acyl group donor is in excess, and so the reactants are present on commencement of the reaction in a molar ratio of first component to second component of 1:500 to 1:200 000, preferably to 1:2000.

Since the entire reaction mixture consists mainly of the reactants, and hence of the first and second components, only very little solvent—if any—may be present in the entire reaction mixture. It is clear on the basis of the above that the second component is not covered by the term "solvent" in the process according to the invention.

Possible solvents would be, for example, ketones, for example methyl isobutyl ketone or cyclohexanone, sterically hindered secondary alcohols such as 2-butyl-1-octanol, methylcyclohexanols, 1-methoxy-2-propanol, butane-2,3-diol, 2-octanol, diacetone alcohol, 2-methyl-2-butanol, and ethers such as 1,4-dioxane, tetrahydrofuran and Varonic APM.

Based on the overall reaction mixture, solvents are present in a maximum total amount of less than 20% by weight, preferably less than 10% by weight, especially less than 5% by weight. The expression "is present in a maximum of less than X % by weight" is equivalent to "has a content of less than X % by weight".

Particular preference is given to conducting the process according to the invention in a solvent-free manner.

Preference is given to conducting the process according to the invention under anhydrous conditions, defined as a water content of not more than 0.100 M, preferably a maximum of 0.010 M and more preferably at a maximum of 0.005 M, detected by the Karl Fischer method.

Preferably, the carboxylic ester hydrolase from the E.C. 3.1.1 enzyme class is one that can be isolated from an organism from the realm of fungi, and carboxylic ester hydrolyses from the E.C. 3.1.1 enzyme class having at least 60%, preferably at least 80%, more preferably at least 90%, especially preferably at least 95%, 98% or 99%, homology at the amino acid level to those that can be isolated from an organism from the realm of fungi.

The enzymes that are homologous at the amino acid level, by comparison with the reference sequence, preferably have at least 50%, especially at least 90%, enzyme activity in propyl laurate units as defined in connection with the present invention.

"Homology at the amino acid level" in the context of the present invention shall be understood here and hereinafter to mean "amino acid identity", which can be determined with the aid of known methods. In general, use is made of special computer programs with algorithms taking into account specific requirements. Preferred methods for determining the identity initially generate the greatest alignment between the sequences to be compared. Computer programs for determining the identity include, but are not limited to, the GCG program package including GAP (Deveroy, J. et al., Nucleic Acid Research 12 (1984), page 387, Genetics Computer Group University of Wisconsin, Medicine (WI), and BLASTP, BLASTN and FASTA (Altschul, S. et al., Journal of Molecular Biology 215 (1990), pages 403-410. The BLAST program can be obtained from the National Center For Biotechnology Information (NCBI) and from other sources (BLAST Handbook, Altschul S. et al., NCBI NLM NIH Bethesda N. Dak. 22894; Altschul S. et al., above).

The person skilled in the art is aware that various computer programs are available for the calculation of similarity or identity between two nucleotide or amino acid sequences. For instance, the percentage identity between two amino acid sequences can be determined, for example, by the algorithm developed by Needleman and Wunsch (J. Mol. Biol. (48): 444-453 (1970)), which has been integrated into the GAP program in the GCG software package (available at www.gcg.com), using either a Blossom 62 matrix or a PAM250 matrix, a gap weight of 16, 14, 12, 10, 8, 6 or 4 and a length weight of 1, 2, 3, 4, 5 or 6. The person skilled in the art will recognize that the use of different parameters will lead to slightly different results, but that the percentage identity between two amino acid sequences overall will not be significantly different. Typically, the Blossom 62 matrix is utilized with employment of the default settings (gap weight: 12, length weight: 1).

In the context of the present invention, an identity of 60% according to the above algorithm means 60% homology. The same applies to higher identities.

Carboxylic ester hydrolases used with particular preference in processes according to the invention are enzymes selected from the group of the lipase from *Thermomyces lanuginosus* with accession number O59952, lipases A and B with accession number P41365 from *Candida antarctica* and the lipase from *Mucor miehei* with accession number P19515, the lipase from *Humicola* sp. with accession number O59952, the lipase from *Rhizomucor javanicus* with accession number 532492, the lipase from *Rhizopus oryzae* with accession number P61872, the lipases from *Candida rugosa* with accession number P20261, P32946, P32947, P3294 and P32949, the lipase from *Rhizopus niveus* with accession number P61871, the lipase from *Penicillium camemberti* with accession number P25234, the lipases from *Aspergillus niger* with accession number ABG73613, ABG73614 and ABG37906 and the lipase from *Penicillium cyclopium* with accession number P61869, and their respective at least 60%, preferably at least 80%, more preferably at least 90%, especially preferably at least 95%, 98% or 99%, homologues at the amino acid level. With regard to homology, reference is made to the definition given above.

Commercial examples, and carboxylic ester hydrolyses that are likewise used with preference in processes according to the invention, are the commercial products Lipozyme TL IM, Novozym 435, Lipozyme IM 20, Lipase SP382, Lipase SP525, Lipase SP523, (all commercial products from Novozymes A/S, Bagsvaerd, Denmark), Chirazyme L2, Chirazyme L5, Chirazyme L8, Chirazyme L9 (all commercial products from Roche Molecular Biochemicals, Mannheim, Germany), CALB Immo Plus™ from Purolite, and Lipase M "Amano", Lipase F-AP 15 "Amano", Lipase AY "Amano", Lipase N "Amano", Lipase R "Amano", Lipase A "Amano", Lipase D "Amano", Lipase G "Amano" (all commercial products from Amano, Japan).

The process according to the invention is preferably conducted at reaction temperatures in the range between 20° C. and 160° C., preferably 35 and 130, especially between 65° C. and 110° C.

The process according to the invention is preferably conducted at a pressure of less than 1 bar, preferably less than 0.5 bar and more preferably less than 0.05 bar.

In an alternative preferred embodiment, the process according to the invention is conducted at a pressure of greater than 1 bar, preferably within a range from 2 bar to 10 bar. In this connection, it is preferable that the reaction mixture is provided with an inert gas; these are preferably selected from the group comprising, preferably consisting of, nitrogen and argon.

US20110077302 and US20110065801 disclose that, when triglycerides are used, for example natural oils, no partial glycerides were observable in significant amounts. It is therefore completely surprising that, in the process according to the invention, when triglycerides are used as the second component, relatively large amounts of mono- and diglycerides are found.

Therefore, the present invention likewise provides a composition comprising

A) at least one sphingolipid of the general formula I

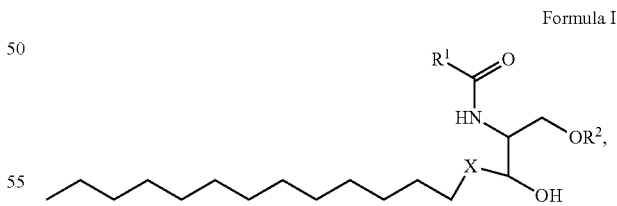

Formula I

B) at least one lysosphingolipid of the general formula II

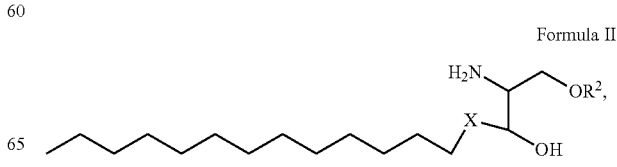

Formula II

C) at least one triglyceride of the general formula III

Formula III

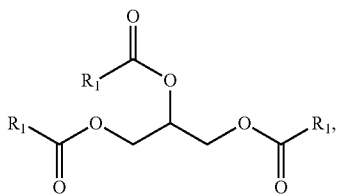

D) at least one diglyceride of the general formula IV

Formula IV

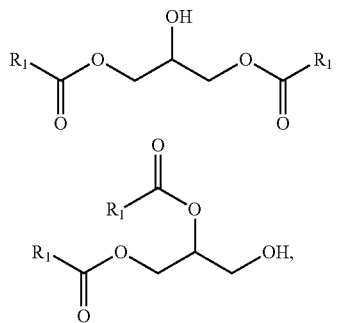

E) at least one monoglyceride of the general formula V

Formula V

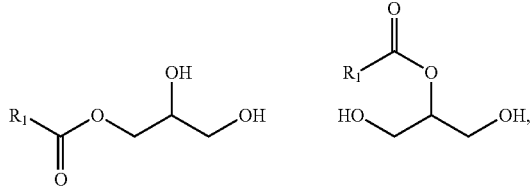

where $R^1$ is the same or different and independently represents a linear or branched alkyl chain having 2 to 55 carbon atoms that optionally contains one or more multiple bonds and/or aromatic or heteroaromatic rings, is optionally interrupted by oxygen atoms or ester or amide functionalities and is optionally substituted by at least one further group selected from alkyl, hydroxyl, keto or amine groups, preferably —$CH_2$—Y—$CH_3$ with Y=a carbon-carbon bond or a linear or branched alkylene chain having 1 to 53, especially 6 to 32, carbon atoms that optionally contains one or more multiple bonds and is optionally substituted by at least one hydroxyl group, $R^2$ is the same or different and independently represents H, phosphocholine, serine, ethanolamine or a sugar, preferably sugar or H, more preferably H, and X represents CH═CH, $CH_2$—$CH_2$ or $CH_2$—HCOH, preferably $CH_2$—$CH_2$, with the proviso that, based on the total composition, the components are present as follows:

A) 30% by weight to 98% by weight, preferably 50% by weight to 90% by weight, more preferably 65% by weight to 85% by weight, B) 0.01% by weight to 60% by weight, preferably 0.1% by weight to 45% by weight, more preferably 0.5% by weight to 10% by weight, C) 0.01% by weight to 60% by weight, preferably 0.01% by weight to 45% by weight, more preferably 0.01% by weight to 10% by weight, D) 0.1% by weight to 30% by weight, preferably 1% by weight to 20% by weight, more preferably 2% by weight to 15% by weight, E) 0.1% by weight to 30% by weight, preferably 1% by weight to 20% by weight, more preferably 2% by weight to 15% by weight.

It has been found that, completely surprisingly, a composition according to the invention as described above can be diluted to a high degree with a triglyceride, and hence with component C), with significant detectability of the activity of the composition as before.

The present invention therefore further provides a composition having a high oil content and comprising A) at least one sphingolipid of the general formula I Formula I

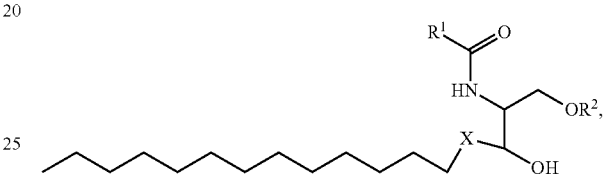

B) at least one lysosphingolipid of the general formula II

Formula II

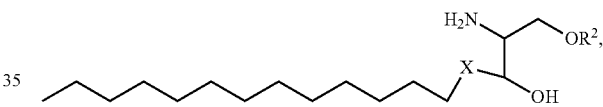

C) at least one triglyceride of the general formula III

Formula III

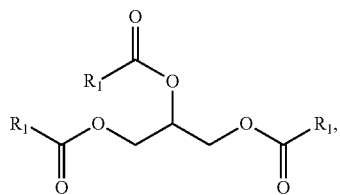

D) at least one diglyceride of the general formula IV

Formula IV

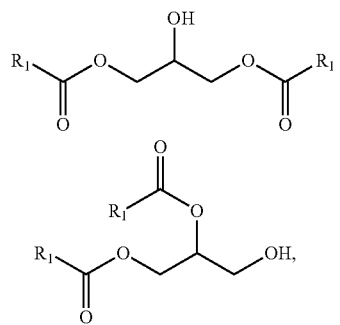

E) at least one monoglyceride of the general formula V

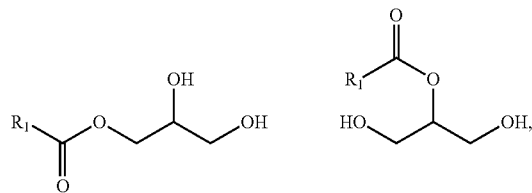

Formula V where $R^1$ is the same or different and independently represents a linear or branched alkyl chain having 2 to 55 carbon atoms that optionally contains one or more multiple bonds and/or aromatic or heteroaromatic rings, is optionally interrupted by oxygen atoms or ester or amide functionalities and is optionally substituted by at least one further group selected from alkyl, hydroxyl, keto or amine groups, preferably —$CH_2$—Y—$CH_3$ with Y=a carbon-carbon bond or a linear or branched alkylene chain having 1 to 53, especially 6 to 32, carbon atoms that optionally contains one or more multiple bonds and is optionally substituted by at least one hydroxyl group, $R^2$ is the same or different and independently represents H, phosphocholine, serine, ethanolamine or a sugar, preferably sugar or H, more preferably H, and X represents CH=CH, $CH_2$—$CH_2$ or $CH_2$—HCOH, preferably $CH_2$—$CH_2$, with the proviso that the components are present in the composition as follows:

A) 30 parts by weight to 98 parts by weight, preferably 50 parts by weight to 90 parts by weight, more preferably 65 parts by weight to 85 parts by weight, B) 0.01 part by weight to 60 parts by weight, preferably 0.1 part by weight to 45 parts by weight, more preferably 0.5 part by weight to 10 parts by weight, D) 0.1 part by weight to 30 parts by weight, preferably 1 part by weight to 20 parts by weight, more preferably 2 parts by weight to 15 parts by weight, E) 0.1 part by weight to 30 parts by weight, preferably 1 part by weight to 20 parts by weight, more preferably 2 parts by weight to 15 parts by weight, and, based on the overall composition, C) 60% by weight to 98% by weight, preferably 71% by weight to 96% by weight, more preferably 81% by weight to 95% by weight.

It is preferable when a composition according to the invention having a high oil content contains components A), B), D) and E) in a total amount of 2% by weight to 29% by weight, preferably 3% by weight to 20% by weight, more preferably 5% by weight to 12% by weight, where the percentages by weight are based on the overall composition having a high oil content.

In a composition preferred in accordance with the invention and in a composition having a high oil content which is preferred in accordance with the invention, $R^2$=H and X=$CH_2$—$CH_2$ and $R^1$ is selected from the group comprising, preferably consisting of, cocyol radicals, palmitoyl radicals, oleyl radicals, linoleyl radicals, linolenyl radicals, ricinoyl radicals, stearyl radicals, erucyl radicals and polyunsaturated fatty acyl radicals.

It has been found that, surprisingly, the composition according to the invention displays a positive effect on skin and hair; therefore, the present invention further provides for the use of the compositions according to the invention and/or of the compositions having a high oil content according to the invention for production of cosmetic formulations.

The present invention further provides for the use of the compositions according to the invention and/or of the compositions having a high oil content according to the invention for retention of skin moisture.

The present invention further provides for the use of the compositions according to the invention and/or of the compositions having a high oil content according to the invention for avoidance of skin dryness.

The present invention further provides for the use of the compositions according to the invention and/or of the compositions having a high oil content according to the invention for fortifying the skin barrier.

The present invention further provides for the use of the compositions according to the invention and/or of the compositions having a high oil content according to the invention for repairing the hair structure after UV stress.

The present invention further provides for the use of the compositions according to the invention and/or of the compositions having a high oil content according to the invention for boosting the CMC complex in the hair.

The present invention further provides for the use of the compositions according to the invention and/or of the compositions having a high oil content according to the invention for protecting the hair, especially from protein degradation.

The present invention further provides for the use of the compositions according to the invention and/or of the compositions having a high oil content according to the invention for stimulating the growth of hair on the scalp.

The present invention further provides for the use of the compositions according to the invention and/or of the compositions having a high oil content according to the invention as antimicrobial agent, especially on the scalp.

The use according to the invention is a cosmetic use.

The examples adduced hereinafter describe the present invention by way of example, without any intention that the invention, the scope of application of which is apparent from the entirety of the description and the claims, be restricted to the embodiments specified in the examples.

The following figures are part of the examples:

FIG. 1: Probability of survival of the individual hairs

FIG. 2: Probability of survival of alkali-straightened hair after treatment with ceramides FIG. 3: Probability of survival of ethnic hair

EXAMPLES

Example 1: Determination of the Specific Activity of the Enzyme Used in PLU

To determine the enzymatic activity in PLU (propyl laurate units), 1-propanol and lauric acid are mixed homogeneously in an equimolar ratio at 60° C. The reaction is started with addition of enzyme and the reaction is timed. Samples are taken from the reaction mixture at intervals, and the content of lauric acid converted is determined by means of titration with potassium hydroxide solution. Enzyme activity in PLU is found from the rate at which 1 g of the enzyme in question synthesizes 1 µmol of propyl laurate per minute at 60° C.; cf. also US20070087418, especially The manufacturer Novozymes, for example, states 10000 PLU/g in its Novozym 435 product data sheet.

Example 2: Reaction of Sphinganine with Olive Oil, Olive Oil-Based Ceramide NG 12 g of olive oil together with 8 g of sphinganine are dissolved in 2.2 g of 2-methyl-2-butanol. The mixture is heated to 100° C., blanketed with nitrogen to 0.05 bar and stirred. On attainment of the reaction temperature, 120 PLU of Novozym 435 are added and stirring is continued. After 24 h, Novozym 435 was filtered off. The reaction mixture thus obtained, based on sphinganine, reached a conversion of >98.5%. After the reaction, the solvent is removed by distillation and the product mixture obtained is used in application tests.

Example 3: Composition Having a High Oil Content 10 g of a composition from Example 2 are dissolved in 90 g of a 1:1 (by weight) mixture of olive oil and castor oil. This gives a composition having a high oil content, containing 10% of a mixture of olive oil-based ceramide NG, glycerol, glycerides and sphinganine with 45% olive oil and 45% castor oil.

Example 4: Reaction of Sphinganine with Castor Oil 25 g of castor oil are mixed with 16 g of sphinganine. The mixture is heated to 100° C., blanketed with nitrogen to 0.05 bar and stirred. On attainment of the reaction temperature, 80 PLU of Novozym 435 (based on sphinganine) are added and stirring is continued. After 24 h, Novozym 435 was filtered off. The reaction mixture thus obtained was blended with 60 ml of castor oil. Based on sphinganine, the reaction reached a conversion of >98.5%.

Example 5: Effect of the Amount of Solvent 12 g of olive oil are mixed with 8 g of sphinganine, and the amount of 2-methyl-2-butanol stated below in the table is added. The mixture is heated to 80° C., blanketed with nitrogen to 0.05 bar and stirred. On attainment of the reaction temperature, the amount of Novozym 435 specified is added and stirring is continued. After 2 h, a sample was taken in each case and analysed by means of GC for the residual sphinganine content. The results show that better conversions can be achieved with decreasing amount of solvent when less enzyme is used. The negative control conducted without addition of solvent and enzyme gave a non-zero conversion.

| Amount of enzyme in PLU/g of sphinganine | 2-Methyl-2-butanol solvent in % | Conversion in % |
|---|---|---|
| 120 | 10 | 26 |
| 25 | 10 | 24 |
| 120 | 1 | 27 |
| 25 | 0 | 28 |

Example 6: Further Synthesis Examples

The general procedure was as described in Example 2 without the use of solvents.

| Name | Acyl donor | Amount of acyl donor in g | Amount of sphinganine in g | Amount of enzyme in PLU/g of sphinganine | Temperature ° C. | Conversion after 24 h in % based on sphinganine |
|---|---|---|---|---|---|---|
| TG1 | Olive oil | 448 | 41 | 200 | 95 | >98 |
| TG2 | Olive oil | 29 | 41 | 200 | 100 | >98 |
|  | Castor oil | 31 |  |  |  |  |
| TG3 | Castor oil | 24 | 16 | 120 | 85 | >98 |
| TG4a | Rapeseed oil | 73 | 25 | 100 | 90 | >95 |
| TG4b | Rapeseed oil | 88 | 10 | 100 | 90 | >95 |
| TG5 | Sesame oil | 10 | 7 | 150 | 90 | >95 |
| TG6 | Palm kernel oil | 56 | 25 | 100 | 90 | >95 |
| TG7a | Palm oil | 70 | 25 | 100 | 90 | >95 |
| TG7b | Palm oil | 84 | 10 | 100 | 90 | >95 |
| TG8 | Almond oil | 10 | 7 | 100 | 90 | >90 |
| TG9 | Sorbitan monooleate | 60 | 50 | 100 | 90 | >70 |
| TG10 | Sorbitan monolaurate | 58 | 50 | 100 | 90 | >70 |
| TG11 | Sorbitan trioleate | 83 | 50 | 100 | 90 | >70 |
| TG12 | Soya oil | 87 | 10 | 100 | 90 | >90 |
| TG13 | Glycol distearate | 50 | 25 | 100 | 90 | >70 |
| TG14 | Cetyltriglyceride | 83 | 50 | 100 | 90 | >90 |

Example 7: Application Data for Skin: Effect on Skin Moisture, Dryness Measured by Flakiness, Skin Barrier Measured by General Condition of Skin In Vivo To determine the skincare properties of the composition having a high oil content from Example 3, an in vivo study was conducted. The sequence of the study was as follows: The subjects each received 2 test formulations that had to be applied to the inside of the underarm twice daily for a duration of 2 weeks. Before commencement of use and after 1 and 2 weeks, a special camera (Visioscan VC 98, Courage & Khazaka, Cologne) was used to take a black and white image of the skin. Using these images, the camera software calculated skin flakiness and skin roughness. The values are calculated from the grey level distribution of the images; therefore, the results have no unit.

The subjects also received a questionnaire for assessment of the care properties of the test formulations. A total of 25 subjects took part in the study.

| Ingredient | Vehicle | Formulation with active ingredient |
|---|---|---|
| Glyceryl Stearate Citrate | 2.00% | 2.00% |
| Cetearyl Alcohol | 1.00% | 1.00% |
| Caprylic/Capric Triglyceride | 4.80% | 4.80% |
| C12-15 Alkyl Benzoate | 4.00% | 4.00% |
| Example 3 (% based on sphingolipid) | | 1.00% |
| Carbomer | 0.20% | 0.20% |
| Ethylhexylglycerin, Phenoxyethanol | 1.00% | 1.00% |
| Sodium hydroxide (10% in water) | 0.70% | 0.70% |
| Water | to 100% | to 100% |

| | Decrease in skin roughness | | Decrease in skin flakiness | |
|---|---|---|---|---|
| | Vehicle | Example 3 | Vehicle | Example 3 |
| After 1 week | −1.58 | −11.08 | −0.0271 | −0.1292 |
| After 2 weeks | −5.61 | −15.04 | −0.0761 | −0.1313 |

| The product reduces the flakiness of the dry skin | The product reduces the flakiness of the dry skin | | The product supplies the skin with sufficient moisture | | My skin condition has improved | |
|---|---|---|---|---|---|---|
| | Vehicle | Example 3 | Vehicle | Example 3 | Vehicle | Example 3 |
| Agree completely | 5.3 | 13.6 | 22.7 | 30.4 | 4.5 | 4.5 |
| Agree | 31.6 | 40.9 | 45.5 | 52.2 | 22.7 | 54.5 |
| Neither agree nor disagree | 57.9 | 40.9 | 31.8 | 17.4 | 72.7 | 40.9 |
| Disagree if anything | 5.3 | 4.5 | 0.0 | 0.0 | 0.0 | 0.0 |
| Disagree completely | 0.0 | 0.0 | 0.0 | 0.0 | 0.0 | 0.0 |

Results of the Subject Questionnaire.

Both skin flakiness and skin roughness were more greatly reduced after application of the formulation comprising the composition having a high oil content from Example 3 than after application of the vehicle formulation. These results were also confirmed by the subjects.

Distinctly higher agreement is seen here with the statements "The formulation reduces the flakiness of the dry skin", "The product supplies the skin with sufficient moisture" and "My skin condition has improved" with the test formulation containing the product from Example 3 than in the case of the vehicle formulation.

Example 8: Application Data for Hair: Repair of UV-Damaged Hair

In the example which follows, the repair effect of a test conditioner containing the product from Example 2 is to be compared to the repair effect of ceramide NP.

Caucasian, undamaged hair was irradiated with UV for 24 h. For this purpose, a UV chamber was used (Dr. Hönle, Sol 2). The hair tresses were irradiated with a power of 910 W/m². Subsequently, the hair was treated as follows:

1. Washing with a test shampoo consisting of sodium lauryl ether sulfate and cocamidopropylbetaine.
2. Application of the test conditioner; the contact time was 5 min. Subsequently, the hair tresses were rinsed under flowing tap water at a temperature of 37° C. for 1 min.
3. Drying of the hair tresses with a hairdryer for 3 minutes.

These three treatment steps were conducted a total of 5×.

Test Formulations:

Shampoo

| Ingredient | Concentration |
|---|---|
| Sodium Laureth Sulfate (28%) | 32.10% |
| Water | 60.50% |
| Cocomidopropyl Betaine (47.5%) | 6.40% |
| Phenoxyethanol, Ethylhexylglycerin | 1.00% |

| Ingredient | Vehicle | Example 2 | Ceramide NP |
|---|---|---|---|
| Ceteareth-25 | 0.50% | 0.50% | 0.50% |
| Cetearyl Alcohol | 4.00% | 4.00% | 4.00% |
| Cetrimonium Chloride | 1.50% | 1.50% | 1.50% |
| Ceramide mixture from Example 2 (% based on sphingolipid) | | 0.10% | |
| Ceramide NP | | | 0.1% |
| Water | to 100% | to 100% | to 100% |
| Phenoxyethanol, Ethylhexylglycerin | 1.00% | 1.00% | 1.00% |
| Lactic acid (10%) | pH 4.0-4.5 | pH 4.0-4.5 | pH 4.0-4.5 |

Test Conditioner for the Repair of UV-Damaged Hair.

For quantification of the repair effect, a hair breakage measurement was conducted (Cyclic Tester, Diastron Limited, UK). In this measurement, individual hairs are extended at a constant force until they break. The number of extension cycles survived is recorded and serves to calculate the probability of survival. About 50 individual hairs were used for each measurement.

FIG. 1 shows that the probability of survival of UV-irradiated hair in the hair breakage test is much smaller than in the case of unirradiated hair (virgin caucasian). Treatment with the ceramide-containing test formulations increased the probability of survival again. It can be seen that the formulation containing the product from Example 2 leads to a higher probability of survival than ceramide NP tested for comparison.

Example 9: Application Data for Hair: Protection from Protein Degradation

Ethnic hair was chemically straightened. For this purpose, a standard formulation based on guanidinium carbonate and calcium hydroxide having a pH of about 12 was used. Subsequently, the hair was treated as follows:
1. Washing with a shampoo consisting of sodium lauryl ether sulfate and cocamidopropylbetaine.
2. Application of the test conditioner; the contact time was 5 min. Subsequently, the hair tresses were rinsed under flowing tap water at a temperature of 37° C. for 1 min.
3. Drying of the hair tresses with a hairdryer for 3 minutes.

These three treatment steps were conducted a total of 5x.
Test Formulation:

| Ingredient | Concentration |
|---|---|
| Sodium Laureth Sulfate (28%) | 32.10% |
| Water | 60.50% |
| Cocomidopropyl Betaine (47.5%) | 6.40% |
| Phenoxyethanol, Ethylhexylglycerin | 1.00% |

Shampoo

| Ingredient | Vehicle | Example 2 | Formulation with ceramide II |
|---|---|---|---|
| Ceteareth-25 | 0.50% | 0.50% | 0.50% |
| Cetearyl Alcohol | 4.00% | 4.00% | 4.00% |
| Cetrimonium Chloride | 1.50% | 1.50% | 1.50% |
| Ceramide mixture from Example 2 (% based on sphingolipid) | | 0.10% | |
| Ceramide II (Sederma) | | | 0.10% |
| Water | to 100% | to 100% | to 100% |
| Phenoxyethanol, Ethylhexylglycerin | 1.00% | 1.00% | 1.00% |
| Lactic acid (10%) | pH 4.0-4.5 | pH 4.0-4.5 | pH 4.0-4.5 |

Test Conditioner

For quantification of the repair effect, a hair breakage measurement was conducted (Cyclic Tester, Diastron Limited, UK). In this measurement, individual hairs are extended at a constant force until they break. The number of extension cycles survived is recorded and serves to calculate the probability of survival. About 50 individual hairs were used for each measurement.

FIG. 2 shows that the probability of survival of alkali-straightened hair in the hair breakage test is much smaller than in the case of unstraightened hair (virgin). Treatment with the ceramide-containing test formulations increased the probability of survival again. It has been found that, surprisingly, the inventive compositions (Example 2) lead to a higher probability of survival than ceramide II (pure sphinganine C18), which is customary for commercial hair care products.

Example 10: Application Data for Hair: Repair of the Hair after Acidic Straightening Ethnic hair was acid-straightened and aftertreated with a conditioner that contained one of the claimed compositions with elevated triglyceride content, consisting of: 10% olive oil-based ceramide (Example 2). For comparison, the process was conducted with a corresponding amount of pure ceramide NG or pure olive oil.

The repair effect and the boosting of the CMC complex by means of Hair fatigue alpha were measured.

Ethnic hair was chemically straightened. For this purpose, an acidic standard formulation having a pH of about 1-2 was used in combination with the use of a straightening iron. Subsequently, the hair was treated as follows:
1. Washing with a shampoo consisting of sodium lauryl ether sulfate and cocamidopropylbetaine.
2. Application of the test conditioner; the contact time was 5 min. Subsequently, the hair tresses were rinsed under flowing tap water at a temperature of 37° C. for 1 min.
3. Drying of the hair tresses with a hairdryer for 3 minutes.

These three treatment steps were conducted a total of 5x.
The test conditioner contained either no active ingredient (vehicle, 1% olive oil, 0.1% ceramide NG) or the claimed compositions having elevated triglyceride content.

| Ingredient | Concentration |
|---|---|
| Sodium Laureth Sulfate (28%) | 32.10% |
| Water | 60.50% |
| Cocomidopropyl Betaine (47.5%) | 6.40% |
| Phenoxyethanol, Ethylhexylglycerin | 1.00% |

Shampoo

| Ingredient | Vehicle | Formulation with Example 3 | Olive oil formulation | Formulation with ceramide NG |
|---|---|---|---|---|
| Ceteareth-25 | 0.50% | 0.50% | 0.50% | 0.50% |
| Cetearyl Alcohol | 4.00% | 4.00% | 4.00% | 4.00% |
| Cetrimonium Chloride | 1.50% | 1.50% | 1.50% | 1.50% |
| Ceramide mixture from Example 3 (% based on sphingolipid) | | 1.00% | | |
| Olive oil | | | 1.00% | |
| Ceramide NG | | | | 0.10% |
| Water | to 100% | to 100% | to 100% | to 100% |
| Phenoxyethanol, Ethylhexylglycerin | 1.00% | 1.00% | 1.00% | 1.00% |
| Lactic acid (10%) | pH 4.0-4.5 | pH 4.0-4.5 | pH 4.0-4.5 | pH 4.0-4.5 |

Test Conditioner

For quantification of the repair effect, a hair breakage measurement was conducted (Cyclic Tester, Diastron Limited, UK). In this measurement, individual hairs are extended at a constant force until they break. The number of extension cycles survived is recorded and serves to calculate the probability of survival. About 50 individual hairs were used for each measurement.

Surprisingly—as shown in FIG. 3—it was found that only the inventive composition could achieve an appropriate repair effect, whereas ceramide NG and olive oil were not able to achieve any repair effect.

Example 11: Application Data on Formulability: Crystal-Free Incorporation into Cosmetic Oils The low solubility of sphingolipids and their high tendency to recrystallize have always made it difficult to stably incorporate them into cosmetic formulations.

It has been found that, surprisingly, the use of the inventive compositions having a high oil content and an elevated triglyceride content leads to distinct simplification of incorporability of the sphingolipids present into cosmetic oils than in the case of prior art sphingolipids.

For this purpose, the solubility temperatures of the sphingolipids were ascertained: A final concentration of 0.1% ceramide in cosmetic oil was chosen. The ceramide compositions were heated and stirred gradually in the cosmetic oils in a beaker on a hotplate. The solubility temperature was attained as soon as the solution was clear. Subsequently, the mixture was stirred at the solubility temperature ascertained for 1 hour. After it had cooled down to room temperature, the formulation was examined.

| Emollient | Polarity | Example 3 | | Pure ceramide NP | |
|---|---|---|---|---|---|
| | | Solubility temperature | Appearance at RT | Solubility temperature | Appearance at RT |
| Octyl-dodecanol | polar | 40° C. | clear | 70° C. | crystals |
| TEGOSOFT APM | polar | 35° C. | clear | 65° C. | crystals |
| TEGOSOFT CT | polar - medium polar | 35° C. | clear | 95° C. | crystals |
| TEGOSOFT M | medium polar | 45° C. | clear | 90° C. | crystals |
| TEGOSOFT OS | non-polar | 50° C. | clear | 100° C. | crystals |
| Mineral Oil | non-polar | 60° C. | cloudy | 110° C. | crystals |

The data show a distinct improvement in incorporability of the inventive compositions having a high oil content into cosmetic oils compared to pure ceramides.

The invention claimed is:

1. A process for preparing sphingolipids of the general formula I

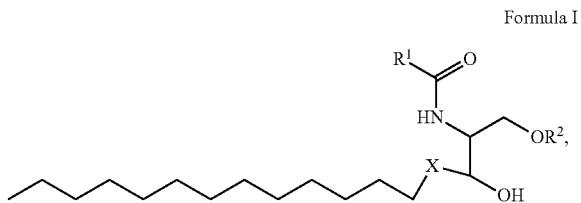

Formula I by reacting a first component, a lysosphingolipid of the general formula II

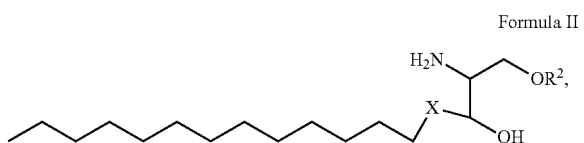

Formula II with a second component selected from an ester based on a polyol having up to 6 carbon atoms,
wherein
the first and second components, based on the overall reaction mixture, account for a total of at least 70% by weight,
and not more than 600 propyl laurate units of at least one carboxylic ester hydrolase from the E.C. 3.1.1 enzyme class per gram of first component are used in the entire reaction mixture, where one propyl laurate unit is defined as the amount of enzyme that synthesizes one µmol of propyl laurate per minute from 1-propanol and lauric acid.

2. The process according to claim 1, wherein the second component selected from an glycerol ester.

3. The process according to claim 1, wherein the second component is selected from glycerol esters.

4. The process according to claim 1, wherein the second component is selected from a glycerol ester based having up to 3 carbon atoms.

5. The process according to claim 1, wherein the first component used is sphinganine with $R^2$=H and X=$CH_2$—$CH_2$, and the second component is selected from the group consisting of coconut fat, palm kernel oil, olive oil, palm oil, argan oil, castor oil, linseed oil and babassu oil.

6. The process according to claim 1, wherein the reactants are present on commencement of the reaction in a molar ratio of first component to second component of 1:0.11 to 1:2000.

7. The process according to claim 1, wherein, based on the overall reaction mixture, the maximum total amount of any solvent present is less than 20% by weight.

8. The process according to claim 1, wherein it is conducted under anhydrous conditions.

9. The process according to claim 1, wherein the carboxylic ester hydrolase is selected from the group of the lipase from *Thermomyces lanuginosus* with accession number 059952, lipases A and B with accession number P41365 from *Candida antarctica* and the lipase from *Mucor miehei* with accession number P19515, the lipase from *Humicola* sp. with accession number 059952, the lipase from *Rhizomucor javanicus* with accession number 532492, the lipase from *Rhizopus oryzae* with accession number P61872, the lipases from *Candida rugosa* with accession number P20261, P32946, P32947, P3294 and P32949, the lipase from *Rhizopus niveus* accession number P61871, the lipase from *Penicillium camemberti* with accession number P25234, the lipases from *Aspergillus niger* with accession number ABG73613, ABG73614 and ABG37906 and the lipase from *Penicillium cyclopium* with accession number P61869, and their respective at least 60% homologues at the amino acid level.

10. The process according to claim 1, wherein the first and second components, based on the overall reaction mixture, account for a total of at least 95% by weight.

11. The process according to claim 1, wherein, based on the overall reaction mixture, the maximum total amount of any solvent present is less than 5% by weight.

12. The process according to claim 1, wherein the carboxylic ester hydrolase is selected from the group of the lipase from *Thermomyces lanuginosus* with accession number 059952, lipases A and B with accession number P41365 from *Candida antarctica* and the lipase from *Mucor miehei* with accession number P19515, the lipase from *Humicola* sp. with accession number 059952, the lipase from *Rhizomucor javanicus* with accession number 532492, the lipase from *Rhizopus oryzae* with accession number P61872, the lipases from *Candida rugosa* with accession number P20261, P32946, P32947, P3294 and P32949, the lipase from *Rhizopus niveus* accession number P61871, the lipase from *Penicillium camemberti* with accession number P25234, the lipases from *Aspergillus niger* with accession number ABG73613, ABG73614 and ABG37906 and the lipase from *Penicillium cyclopium* with accession number P61869, and their respective at least 95% homologues at the amino acid level.

* * * * *

UNITED STATES PATENT AND TRADEMARK OFFICE
CERTIFICATE OF CORRECTION

PATENT NO. : 11,155,842 B2
APPLICATION NO. : 16/355981
DATED : October 26, 2021
INVENTOR(S) : Marrit Friederike Eckstein et al.

It is certified that error appears in the above-identified patent and that said Letters Patent is hereby corrected as shown below:

In the Claims

Column 18,
Line 26, in Claim 9, "059952, lipases A and B" should read -- O59952, lipases A and B --.
Line 29, in Claim 9, "number 059952, the lipase" should read -- number O59952, the lipase --.
Line 30, in Claim 9, "number 532492, the lipase" should read -- number S32492, the lipase --.
Line 51, in Claim 12, "059952, lipases A and B" should read -- O59952, lipases A and B --.
Line 54, in Claim 12, "number 059952, the lipase" should read -- number O59952, the lipase --.
Line 55, in Claim 12, "number 532492, the lipase" should read -- number S32492, the lipase --.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*